United States Patent
Klumpe et al.

(10) Patent No.: US 9,073,836 B2
(45) Date of Patent: Jul. 7, 2015

(54) PROCESS FOR PREPARING ALLYL ALCOHOL ALKOXYLATES

(75) Inventors: Markus Klumpe, Mannheim (DE); Thomas Ostrowski, Mannheim (DE); Matthias Zipplies, Neustadt (DE)

(73) Assignee: BASF SE, Ludwigshafen (DE)

( * ) Notice: Subject to any disclaimer, the term of this patent is extended or adjusted under 35 U.S.C. 154(b) by 567 days.

(21) Appl. No.: 13/197,336

(22) Filed: Aug. 3, 2011

(65) Prior Publication Data

US 2012/0035381 A1 Feb. 9, 2012

Related U.S. Application Data

(60) Provisional application No. 61/370,121, filed on Aug. 3, 2010.

(51) Int. Cl.
C07C 41/03 (2006.01)
C08G 65/26 (2006.01)

(52) U.S. Cl.
CPC ............ *C07C 41/03* (2013.01); *C08G 65/2696* (2013.01)

(58) Field of Classification Search
USPC ........................................................ 568/616
See application file for complete search history.

(56) References Cited

U.S. PATENT DOCUMENTS

| 4,412,926 A | 11/1983 | Nieh et al. |
| 6,143,821 A | 11/2000 | Houben |
| 2005/0261457 A1 | 11/2005 | Falk et al. |
| 2011/0224397 A1 | 9/2011 | Ostrowski et al. |

FOREIGN PATENT DOCUMENTS

| DE | 195 43 368 A1 | 5/1997 |
| DE | 10 2006 048 017 A1 | 4/2008 |
| DE | 102006048017 A1 * | 4/2008 |
| WO | WO 2004/026468 A1 | 4/2004 |

OTHER PUBLICATIONS

U.S. Appl. No. 13/322,743, filed Nov. 28, 2011, Klumpe, et al.
U.S. Appl. No. 13/387,540, filed Jan. 27, 2012, Schopohl, et al.
U.S. Appl. No. 61/311,782, filed Mar. 9, 2010, Ostrowski, et al.
International Search Report Issued Nov. 3, 2011, in PCT/EP2011/062778 with English translation of category of cited documents.

* cited by examiner

*Primary Examiner* — Rosalynd Keys
(74) *Attorney, Agent, or Firm* — Oblon, McClelland, Maier & Neustadt, L.L.P.

(57) ABSTRACT

A process for preparing polyether alcohols by reacting one or more unsaturated starters having at least one active hydrogen atom per molecule with one or more alkylene oxides in the liquid phase in the presence of a basic catalyst in a reactor, wherein the one or more alkylene oxides are introduced into the reactor in such a way that the concentration of unreacted alkylene oxide in the liquid reaction mixture in the reactor is increased as far as possible with increasing degree of addition of the alkylene oxide onto the starter, with the proviso that the temperature at the end of a runaway reaction is at any point in time at least 100 K below the onset temperature of the decomposition reaction of the liquid reaction mixture, is proposed.

7 Claims, No Drawings

PROCESS FOR PREPARING ALLYL ALCOHOL ALKOXYLATES

This patent application claims the benefit of pending U.S. provisional patent application Ser. No. 61/370,121 filed Aug. 3, 2010 incorporated in its entirety herein by reference The invention relates to a process for preparing polyether alcohols by reacting one or more unsaturated starters having at least one active hydrogen atom per molecule with one or more alkylene oxides in the presence of a basic catalyst.

Polyether alcohols based on unsaturated starters, i.e. starters having one or more terminal or internal double bonds, are used, inter alia, for producing polyurethane foam stabilizers, for the synthesis of demulsifiers for crude oil dewatering or for producing flow improvers for building materials such as concrete.

The polyether alcohols in question are preferably allyl or methallyl alcohol alkoxylates which are prepared by alkoxylation of allyl or methallyl alcohol, essentially using ethylene oxide and/or propylene oxide, in the presence of basic catalysts. The unsaturated starter alcohol, for example allyl alcohol or methallyl alcohol, is placed in a reaction vessel and the amount of catalyst, usually an alkali metal hydroxide or an alkali metal alkoxide, necessary for a sufficiently rapid reaction is introduced. For this purpose, it is advantageous to use a solid catalyst since, owing to the boiling point of allyl alcohol of 95° C., removal of water by simple distillation is not possible. However, since solid alkali metal hydroxides still comprise water (thus, for example, potassium hydroxide is generally only available as a solid having a potassium hydroxide content of 88% by weight, based on the total weight), diols are formed as undesirable by-products because of the water content in the alkali metal hydroxide. This disadvantage can be overcome by using alkoxides as catalysts.

After introduction of the catalyst, the alkoxylation reactor is made inert, generally by means of nitrogen, heated to the reaction temperature, which in the case of unsaturated starters, is in the range from about 80 to 120° C., and the alkylene oxides are introduced, with both block and mixed oxide methods being customary. Alkylene oxides used are in particular ethylene oxide and propylene oxide but also 1,2-butylene oxide, isobutylene oxide, pentene oxide, decene oxide and styrene oxide.

A problem is that unsaturated starters in the presence of bases as are used for the above-described alkoxylations undergo, at relatively high temperatures, secondary reactions which are so strongly exothermic that they represent a safety risk.

Dynamic differential calorimetric measurements on an unsaturated starter, in particular allyl alcohol and methallyl alcohol, in basic medium, in particular at concentrations of 0.07 mol of sodium or potassium hydroxide per mol of unsaturated starter, have shown that exothermic decomposition temperatures having high reaction enthalpies above 200 kJ/kg occur at onset temperatures as low as from 145 to 170° C. Here, the onset temperature is the temperature at which the commencement of evolution of heat is detectable by dynamic differential calorimetric measurement; for reasons of comparability of the measurements, these are always based on a heating rate of 2.5 K/min.

In reactor operation, the technical rules for plant safety, TRAS for short, have to be adhered to. TRAS 410, 04/2007 version, page 8, prescribes, for the safe operation of reactors, a spacing of the final temperature of a reaction mixture in the event of a runaway reaction in the reactor from the onset temperature of an exothermic decomposition reaction of 100 K so that an adiabatic induction time of 24 hours is ensured.

For the present purposes, the adiabatic induction time is the time within which the reaction mixture undergoes further reactions, generally decompositions, which are associated with strong gas formation and as a result can lead to a pressure buildup and under some circumstances to rupture of the reactor if the safety valves cannot remove the energy. Before this decomposition occurs, the temperature has to be lowered sufficiently by means of suitable measures. It is assumed that it is possible for an operator to initiate appropriate measures (drainage, emergency cooling by means of additional pumps which may in the event of total utilities failure be independent of the power grid, etc.) within the 24 hours mentioned. Induction times shorter than 24 hours are permissible when other suitable measures are present, for example special cooling facilities, quenching containers or appropriately dimensioned pressure release facilities. It has to be taken into account here that, in particular, ethylene oxide which can be present in unreacted form in the reaction mixture is a carcinogenic material of category II and must not be released into the environment and accordingly makes it necessary to provide an appropriately dimensioned offgas scrub or incineration.

However, the very low permissible accumulation of alkylene oxides determined by the limitation of the adiabatic final temperature in the case of a runaway reaction, for example in the event of a cooling failure, leads to a low reaction rate and thus to long alkylene oxide introduction times since the reaction rate is linearly dependent on the alkylene oxide concentration.

The patent literature often describes alkoxylation processes of unsaturated starters for which very high alkylene oxide concentrations are recommended without safety aspects being addressed. However, specific, complicated safety measures, for example special cooling facilities, quenching containers or appropriately dimensioned pressure release facilities, are necessary for the processes described therein to be carried out safely.

Thus, according to Example 1 in U.S. Pat. No. 4,412,926, 5 mol of ethylene oxide per mol of allyl alcohol are introduced at from 120 to 130° C. and a maximum pressure of 4.1 bar. Assuming an ethylene oxide solubility coefficient of 0.517 (dimensionless) at 125° C. and an initial addition of 1 mol of ethylene oxide mol of allyl alcohol, the free ethylene oxide concentration in the liquid phase is about 9%. The amount of ethylene oxide in the liquid is calculated according to the equation $$\text{Amount of ethylene oxide}_{liquid} = \text{total amount}_{liquid} \cdot \text{solubility coefficient/ethylene oxide vapor pressure} \cdot \text{ethylene oxide partial pressure}.$$

In the case of a runaway reaction, this gives, assuming an adiabatic reaction, a final temperature of the reaction mixture of 219° C., which is above the first onset temperature of 165° C. and is also only about 60 K below the second onset temperature of 280° C.; the requirements of TRAS 410 are therefore not satisfied for allyl alcohol alkoxylated with 1 mol of ethylene oxide.

In DE 195 43 368, Example 1, 5 mol of ethylene oxide are likewise introduced per mol of allyl alcohol at 140° C. and a maximum pressure of from 3 to 6 bar. This gives, depending on the reactor pressure, a free alkylene oxide concentration in the range from 3 to 9%, which in the event of a runaway reaction leads to adiabatic final temperatures of from 177 to 237° C. Taking into account the abovementioned, known values for the first and second onset temperatures of the decomposition reaction of allyl alcohol alkoxylated with 1 mol of ethylene oxide (165° C. and 280° C., respectively), the temperatures reached at the end of the runaway reaction are in this case too above the values recommended by the TRAS 410.

A further problem when using unsaturated starters, in particular allyl alcohol or methallyl alcohol, is that these readily rearrange in a basic medium. Thus, allyl alcohol easily rearranges to form cis-propenyl. However, the allyl groups which have rearranged to form cis-propenyl compounds display an undesirable reaction behavior in the subsequent syntheses. Since the rearrangement of allyl to cis-propenyl groups is strongly accelerated by elevated temperatures, this can only be avoided or reduced by working at relatively low temperatures. However, low reaction temperatures impair the economics of the process.

Attempts have therefore been made to find solutions which make available safe processes for the alkoxylation of unsaturated starters and at the same time ensure good economics and a high product quality.

DE-A1 10 2006 048 017 proposes a two-stage process in which not more than 10 mol of alkylene oxide per mol of unsaturated starter are reacted at a catalyst concentration of not more than 0.0085 mol of basic catalyst per mol of unsaturated starter in a first process stage and the reaction product from the first stage is reacted with further alkylene oxide at a catalyst concentration of at least 0.010 mol of basic catalyst per mol of unsaturated starter in a second or optionally further process stage(s).

However, this way of carrying out the process has the disadvantage of a poorer space-time yield because the second process stage can be carried out only after complete reaction of the alkylene oxides introduced in the first stage and this will, in particular because of the very low catalyst concentration in the first stage, take a very long time, with the consequence that the concentration of by-products can also be elevated.

In the light of the above, it was an object of the invention to provide a technically simple process for alkoxylating unsaturated starters, which at the same time satisfies the requirements of increased reactor safety, a high space-time yield and a high product quality.

This object is achieved by a process for preparing polyether alcohols by reacting one or more unsaturated starters having at least one active hydrogen atom per molecule with one or more alkylene oxides in the liquid phase in the presence of a basic catalyst in a reactor, wherein the one or more alkylene oxides are introduced into the reactor in such a way that the concentration of unreacted alkylene oxide in the liquid reaction mixture in the reactor is increased as far as possible with increasing degree of addition of the alkylene oxide onto the starter, with the condition that at any point in time the temperature at the end of a runaway reaction is at least 100 K below the onset temperature of the decomposition reaction of the liquid reaction mixture.

It has been found that the space-time yield of the alkoxylation reaction of unsaturated starters can be increased while simultaneously ensuring a high product quality and safe plant operation by regulating the introduction of the one or more alkylene oxides into the alkoxylation reactor as a function of the degree of alkoxylation of the unsaturated starter in such a way that this is set to as high as possible a value at any point in time, while always ensuring that the temperature at the end of a runaway reaction is at least 100 K below the onset temperature of the decomposition reaction of the liquid reaction mixture.

The onset temperatures of the decomposition reaction of alkoxylated unsaturated starters depend on the degree of addition of the alkylene oxide onto the unsaturated starter.

The following table shows results of DSC measurements at a heating rate of 2.5 K/min for allyl alcohol at different degrees of addition of ethylene oxide or propylene oxide onto the allyl alcohol:

| EO [mol/mol$_{allyl}$] | PO | KOH [%] | Onset temperature [° C.] | ΔH [J/g] |
|---|---|---|---|---|
| 0 | 0 | 8.71 | 240 | 720 |
| 1 | 0 | 5.15 | 280 | 620 |
| 2 | 0 | 3.65 | 300 | 610 |
| 4 | 0 | 2.31 | 300 | 780 |
| 8 | 0 | 1.33 | 310 | 1040 |
| 12 | 0 | 0.94 | 320 | 760 |
| 0 | 4 | 1.87 | 305 | 430 |
| 0 | 8 | 1.05 | 320 | 510 |
| 0 | 12 | 0.73 | 310 | 440 |
| 2 | 2 | 2.07 | 315 | 540 |

The table shows that, depending on the degree of addition of the alkylene oxide onto the allyl alcohol, decomposition reactions associated with high reaction enthalpies of >200 kJ/kg commence at difference onset temperatures which increase with increasing degree of alkoxylation.

Comparison of ethoxylates and propoxylates having degrees of addition onto the starter (degrees of alkoxylation) in the range from 4 to 12 mol of alkylene oxide per mol of allyl alcohol shows that there are no significant differences between the onset temperatures of ethoxylates and propoxylates. This is also confirmed by DSC measurement on the mixed oxide allyl alcohol alkoxylate (allyl alcohol ethoxylate/propoxylate): here, the onset temperature measured is 315° C. and is thus close to that of the pure ethoxylates (300° C. for an allyl ethoxylate having 4 mol of ethylene oxide per mol of allyl alcohol) or propoxylate (305° C. for the addition product of 4 mol of propylene oxide onto 1 mol of allyl alcohol).

An unalkoxylated allyl alcohol itself has an onset temperature of only 240° C. in the presence of potassium hydroxide. In order to comply with the recommendations of the TRAS 410, the free alkylene oxide accumulated in the reaction mixture would in the case of a runaway reaction in the reactor, i.e. in the event of a cooling failure, therefore have to be such that the maximum temperature of 140° C. (i.e. 100 K below the onset temperature of the decomposition reaction) is not exceeded in the runaway reaction.

The invention therefore makes use of the surprising recognition that an increasing degree of alkoxylation is accompanied by an increase in the onset temperature and that the reaction enthalpy of the decomposition reaction decreases again above a particular degree of alkoxylation.

For the present purposes, unsaturated starters having at least one active hydrogen atom per molecule are substances having one or more terminal or internal double bonds, in particular ether amines or ether alcohols having at least one ethylenic double bond per molecule, in particular ether alcohols of the general formula I

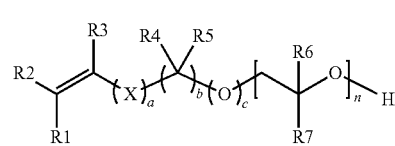

where:

R1-R7 are each, independently of one another, H, methyl, ethyl, propyl or another aliphatic or aromatic radical,

X=O, S, where a=0 AND b=an integer from 0 to 5 AND c=1 AND 0>n>100

OR where a=1 AND b=an integer from 0 to 5 AND c=0 and 0>n>100.

As unsaturated starters, preference is in the present case given to using allyl alcohol, methallyl alcohol, isoprenol, 3-methyl-3-buten-1-ol, 3-methyl-2-buten-1-ol, 2-methyl-3-buten-2-ol, hydroxybutyl vinyl ether, 3,4-dihydroxy-1-butene.

Particular preference is given to using allyl alcohol or methallyl alcohols as unsaturated starters.

In addition, it is also possible to use starters having at least one active hydrogen atom per molecule and no double bonds in addition to the unsaturated starters. However, the concentration of unsaturated starters should be at least 40% by weight, preferably at least 60% by weight, particularly preferably at least 90% by weight, based on the total weight of the starter mixture of unsaturated and saturated starters.

Starters without unsaturated groups which can be additionally comprised in the starter mixture can, in particular, be selected from the following listing: methanol, ethanol, propanol, n-butanol, isobutanol, t-butanol, hexanol, $C_{12}/C_{14}$-alcohol, $C_9C_{11}$-oxo alcohols, $C_{13}C_{15}$-oxo alcohols, tridecanol N, $C_{16}/C_{18}$-tallow fatty alcohols, $C_{12}C_{14}$-alcohols, $C_{14}C_{16}$-alcohols, castor oil, hydrogenated castor oil, 12-hydroxystearic acid, nonylphenol, ocenol, 2-propylheptanol, 2-ethylhexanol, ethylene glycol, diethylene glycol, triethylene glycol, butyl diglycol, butyl triglycol, butyl glycol, propylene glycol, dipropylene glycol, dipropylene glycol monobutyl ether, tripropylene glycol, octylphenol, ethylendiamine, glycerol, trimethylolpropane, phenyl glycol, phenyl diglycol, β-naphthol, isodecanol, methyl glycol, methyl diglycol, bisphenol-A, phenol, o-cresol, m-cresol and p-cresol.

As catalysts, it is possible to use alkali metal hydroxides such as KOH, NaOH, CsOH, alkaline earth metal hydroxides such as $Ca(OH)_2$, $Sr(OH)_2$, or alkali metal alkoxides such as KOMe, NaOMe, K-t-BuO, Na-t-BuO. It is also possible to use mixtures of the abovementioned catalysts. The catalysts can be used either as solids or as solutions or suspensions, with the solvents optionally being removed. It is also possible to add only part of the catalyst at the beginning of the reaction and introduce further catalysts in one or more portions at a later point in time, with the catalysts being able to be identical or different and the solvents being able, depending on requirements, to be removed or left in the reaction mixture.

Preference is given to using sodium hydroxide or potassium hydroxide as a solid or in aqueous solution as basic catalyst.

As alkylene oxide, preference is given to using ethylene oxide and/or propylene oxide.

To carry out the process of the invention, the concentration of unreacted alkylene oxide in the liquid reaction mixture in the reactor and also the current degree of addition of the alkylene oxide onto the unsaturated starter, in particular allyl alcohol or methallyl alcohol, has to be known during the entire introduction of oxide.

To determine the concentration of unreacted alkylene oxide in the liquid reaction mixture in the reactor, it is possible to use all known methods:

Thus, it is possible to measure the concentration of unreacted alkylene oxide in the liquid phase directly, for example by means of optical methods such as NIR, IR or Raman spectroscopy. However, such measurements are very complicated and the measuring instruments, in particular on-line IR and on-line Raman spectrometers, are relatively sensitive, so that these methods of measurement tend to be suitable for laboratory or pilot plant use but not for industrial plants.

The concentration of unreacted alkylene oxide in the liquid phase can also be determined indirectly, for example via the viscosity of the liquid phase since unreacted alkylene oxide reduces the viscosity of the reaction mixture. However, complicated calibrations are necessary for this purpose since the viscosity of the liquid phase increases with increasing degree of alkoxylation.

A further indirect method of measurement is density measurement, for example by means of mass flow meters, with the density being able to be measured using the coriolis force principle in a bypass through which the reaction mixture flows.

However, in this case, too, the dependence of the density on the degree of alkoxylation has to be taken account, as indicated above in relation to the viscosity measurement.

Further indirect methods of measurement which are based on the determination of physical parameters are measurement of the speed of sound, the indices of refraction or the dielectric constants.

A further indirect method of determining the concentration of unreacted alkylene oxide is gas-chromatographic analysis of the gas phase in the reactor. Starting from the gas phase composition determined by gas chromatography and taking into account the total pressure in the reactor, the partial pressure of alkylene oxide in the gas phase is calculated and, taking into account the solubility coefficient of alkylene oxide, the gas phase concentration of the latter can be derived.

Gas chromatographs are available in appropriately robust designs for use in large-scale manufacture.

A further method of determining the free alkylene oxide concentration which is simple to use and can be employed universally has been found to be measurement of the gas pressure in the reactor, from which it is possible to calculate the concentration of unreacted alkylene oxide in the liquid reaction mixture when the solubility coefficient of the alkylene oxides in the reaction mixture is known and the compression pressure of the nitrogen has been calculated.

By increasing the permissible reactor pressure as a function of the degree of addition of the alkylene oxide onto the starter and thus the onset temperature for the decomposition reaction taking into account the change in the nitrogen partial pressure as a result of the compression of the inert gas pressure initially set as far as possible, taking care that at any point in time the temperature at the end of a possible runaway reaction is at least 100 K below the onset temperature of the decomposition reaction of the liquid reaction mixture, the invention provides a simple way of carrying out the alkoxylation at a reaction rate which is maximized while ensuring safe operation.

The process of the invention is thus preferably carried out with the introduction of the one or more alkylene oxides being regulated by continuously measuring the gas pressure in the reactor, calculating the partial pressure of the one or more alkylene oxides therefrom, taking into account the inert gas pressure set before the beginning of the reaction, and calculating the concentration of unreacted alkylene oxide in the liquid reaction mixture via the solubility of the one or more alkylene oxides in the liquid reaction mixture and calculating the temperature to be expected at the end of a runaway reaction from the concentration of unreacted alkylene oxide in the liquid reaction mixture and the degree of addition of the alkylene oxide onto the starter alcohol calculated on the basis of the ratio of alkylene oxide introduced and initially charged starter calculated at the respective point in time and regulating the flow of the one or more alkylene oxides introduced in such a way that the temperature to be expected at the end of a runaway reaction is at least 100 K below the onset temperature of the decomposition reaction of the reaction mixture.

The introduction of the one or more alkylene oxides into the reactor is preferably carried out in such a way that the concentration of unreacted alkylene oxide in the liquid reaction mixture in the reactor is increased as far as possible with increasing degree of addition of the alkylene oxide onto the starter alcohol, with it having to be ensured that at any point in time the temperature at the end of a runaway reaction is at least 50 K below the onset temperature of the decomposition reaction of the liquid reaction mixture.

Example

The preparation of a product of allyl alcohol and EO having a degree of alkoxylation of 10 mol of EO per mol of allyl alcohol is carried out as follows.

89 g of allyl alcohol are introduced at room temperature into a 1 l stainless steel autoclave. 6.16 g of KOH flakes (88% pure) are subsequently introduced. The reactor is closed and evacuated at room temperature to a pressure of 100 mbar (abs). The reactor is subsequently pressurized to atmospheric pressure with nitrogen and evacuated again to 100 mbar (abs). The vacuum is again broken using nitrogen. The reactor is heated to 90° C. A pressure of about 0.9 bar (gauge) is established as a result. 660 g of ethylene oxide are subsequently introduced at 95° C. During the addition, the permissible EO partial pressure, which is given by the difference between reactor pressure and nitrogen partial pressure (calculated via the compression resulting from introduction of EO), is gradually increased so that a final pressure of 7.2 bar (gauge) results. The total time of introduction was 6.2 hours. This gives 749.5 g of the product allyl alcohol+10 EO having an OHN of 117.2 mg KOH/g.

Comparative Example

The experiment was repeated as described above but the permissible reactor pressure was gradually increased to only 4.6 bar (gauge). The introduction time was 8.5 hours.

The product had an OH number of 116.9 mg KOH/g.

The example thus demonstrates that in a process carried out according to the invention, the space-time yield can be increased considerably while at the same time ensuring a high product quality.

The invention claimed is:

1. A process for preparing polyether alcohols by reacting one or more unsaturated starters having at least one active hydrogen atom per molecule with one or more alkylene oxides in the liquid phase in the presence of a basic catalyst in a reactor, wherein the one or more alkylene oxides are introduced into the reactor in such a way that the concentration of unreacted alkylene oxide in the liquid reaction mixture in the reactor is increased as far as possible with increasing degree of addition of the alkylene oxide onto the starter, with the proviso that at any point in time the temperature at the end of a runaway reaction is at least 100 K below the onset temperature of the decomposition reaction of the liquid reaction mixture.

2. The process according to claim 1, wherein the unsaturated starter is allyl alcohol or methallyl alcohol.

3. The process according to claim 1, wherein the alkylene oxide is ethylene oxide and/or propylene oxide.

4. The process according to claim 1, wherein the basic catalyst is an alkali metal hydroxide or an alkali metal alkoxide.

5. The process according to claim 4, wherein the basic catalyst is sodium hydroxide or potassium hydroxide.

6. The process according to claim 1, wherein the introduction of the one or more alkylene oxides into the reactor is carried out in such a way that the concentration of unreacted alkylene oxide in the liquid reaction mixture in the reactor is increased as far as possible with increasing degree of addition of the alkylene oxide onto the starter alcohol, with the proviso that at any point in time the temperature at the end of a runaway reaction is at least 50 K below the onset temperature of the decomposition reaction of the liquid reaction mixture.

7. The process according to claim 1, wherein the introduction of the one or more alkylene oxides is regulated by continuously measuring the free alkylene oxide concentration in the liquid phase in the reactor and on this basis regulating the flow of the one or more alkylene oxides introduced in such a way that the temperature to be expected at the end of a runaway reaction is at least 100 K below the onset temperature of the decomposition reaction of the reaction mixture.

* * * * *